(12) United States Patent
Gillis et al.

(10) Patent No.: US 8,929,969 B2
(45) Date of Patent: Jan. 6, 2015

(54) CATHETER ASSEMBLY AND ASSOCIATED METHOD

(75) Inventors: Edward M. Gillis, San Jose, CA (US); Christine Beltran, San Jose, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 219 days.

(21) Appl. No.: 12/533,264

(22) Filed: Jul. 31, 2009

(65) Prior Publication Data

US 2010/0261990 A1    Oct. 14, 2010

Related U.S. Application Data

(60) Provisional application No. 61/169,269, filed on Apr. 14, 2009.

(51) Int. Cl.
| | |
|---|---|
| *A61B 5/04* | (2006.01) |
| *A61M 25/00* | (2006.01) |
| *A61B 5/042* | (2006.01) |
| *A61B 8/14* | (2006.01) |
| *A61N 1/00* | (2006.01) |

(52) U.S. Cl.
CPC .......... *A61M 25/0009* (2013.01); *A61B 5/0422* (2013.01); *A61M 25/0043* (2013.01)
USPC ........................... 600/381; 600/466; 607/122

(58) Field of Classification Search
CPC ................. A61B 18/1492; A61B 2017/00044; A61B 2017/22038; A61B 2018/0016; A61B 2018/00577; A61B 5/6851
USPC .............. 600/372–374, 381, 466; 606/32–52; 607/122
See application file for complete search history.

(56) References Cited

U.S. PATENT DOCUMENTS

| | | | | |
|---|---|---|---|---|
| 3,590,822 | A * | 7/1971 | Ackerman | 607/122 |
| 4,289,138 | A * | 9/1981 | Halvorsen | 600/375 |
| 5,324,326 | A * | 6/1994 | Lubin | 607/122 |
| 5,827,278 | A * | 10/1998 | Webster, Jr. | 606/41 |
| 5,938,694 | A * | 8/1999 | Jaraczewski et al. | 607/122 |
| 6,356,791 | B1 * | 3/2002 | Westlund et al. | 607/115 |
| 6,926,711 | B2 * | 8/2005 | Lentz et al. | 606/21 |
| 2003/0199836 | A1 * | 10/2003 | Tiernan et al. | 604/264 |
| 2005/0070887 | A1 * | 3/2005 | Taimisto et al. | 606/41 |
| 2007/0043390 | A1 * | 2/2007 | Neilan | 606/200 |
| 2008/0161774 | A1 | 7/2008 | Hastings et al. | |
| 2009/0043186 | A1 | 2/2009 | Jung et al. | |

* cited by examiner

*Primary Examiner* — Linda Dvorak
*Assistant Examiner* — Brian M Antiskay
(74) *Attorney, Agent, or Firm* — Christopher & Weisberg, P.A.

(57) ABSTRACT

A catheter assembly for use in an anatomy can include an elongated body, which can have a proximal end and a distal end. The body can also define a lumen from the proximal end to the distal end. The assembly can include at least one electrode, which can be coupled to the distal end to sense an electrical activity within the anatomy. The assembly can include a core wire, which can be received within the lumen from the proximal end to the distal end. The core wire can be configured to move the distal end from a first configuration to a second configuration. The assembly can also include a necked portion, which can be formed between the proximal end and the distal end to provide increased stiffness to the distal end of the body.

11 Claims, 3 Drawing Sheets

CATHETER ASSEMBLY AND ASSOCIATED METHOD

CROSS-REFERENCE TO RELATED APPLICATION

This application claims the benefit of U.S. Provisional Application No. 61/169,269, filed on Apr. 14, 2009. The entire disclosure of the above application is incorporated herein by reference.

INTRODUCTION

The human anatomy includes many types of tissue that can either voluntarily or involuntarily, perform certain functions. However, after disease or injury, certain tissues may no longer operate within general anatomical norms. For example, after disease, injury, age, or combinations thereof, the heart muscle may begin to experience certain failures or deficiencies. In one example, the heart muscle may begin to develop an abnormal rhythm, which can be generally referred to as a cardiac arrhythmia.

Currently, many different devices and methods have been developed for both diagnosis and for treatment of the various symptoms of cardiac arrhythmias. In one example, in order to treat an abnormal heart rhythm involving the atria, or atrial fibrillation, devices and methods can be employed to electrically isolate a portion of the heart muscle from the atria, such as isolating one or more of the pulmonary veins from the left atrium. Prior to or after isolating one or more of the pulmonary veins, it may be desirable to determine the electrical activity within the heart muscle.

SUMMARY

The present disclosure relates to medical systems, in particular to a system and method for an improved catheter assembly for sensing electrical activity.

In this regard, provided is a catheter assembly for use in an anatomy. The assembly can include an elongated body, which can have a proximal end and a distal end. The body can also define a lumen from the proximal end to the distal end. The assembly can include at least one electrode, which can be coupled to the distal end to sense an electrical activity within the anatomy. The assembly can include a core wire, which can be received within the lumen from the proximal end to the distal end. The core wire can be configured to move the distal end from a first configuration to a second configuration. The assembly can also include a necked portion, which can be formed between the proximal end and the distal end to provide increased stiffness to the distal end of the body.

In further exemplary embodiments of the present disclosure, a catheter assembly for use in an anatomy is provided. The assembly can include an elongated body, which can have a proximal end, a distal end and a body diameter. The body can also define a lumen from the proximal end to the distal end. The assembly can include at least one electrode, which can be coupled to the distal end to sense an electrical activity within the anatomy. The assembly can include a core wire, which can be received within the lumen from the proximal end to the distal end. The core wire can be configured to move the distal end from a first configuration to a second configuration. The assembly can also include at least one necked portion, which can be formed between the proximal end and the distal end to provide increased stiffness to the distal end of the body. The at least one necked portion can include a necked diameter that is smaller than the body diameter of the elongated body.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
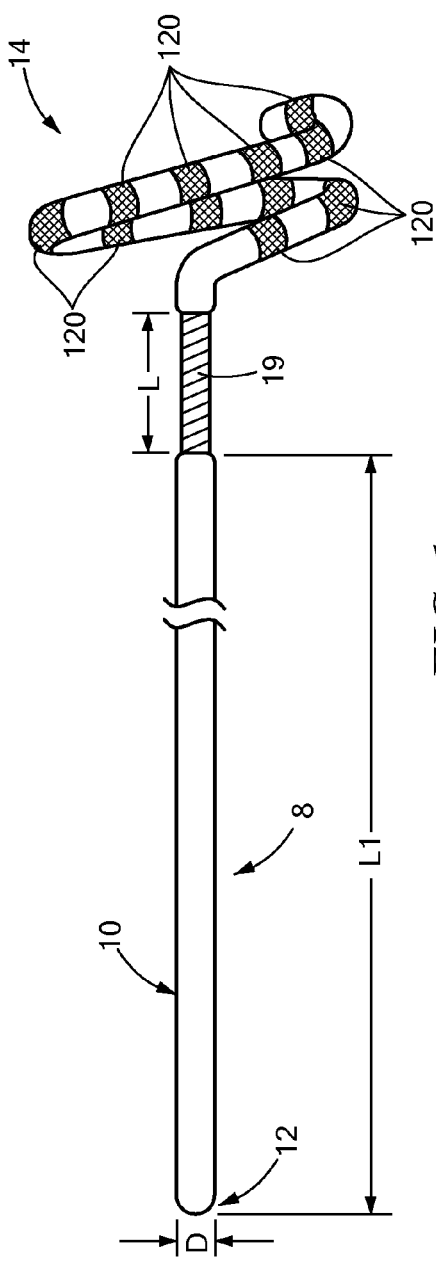
FIG. 1 is a schematic illustration of an exemplary catheter assembly for sensing electrical activity in a first configuration.

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for an improved catheter assembly. It should be noted, however, that the present teachings could be applicable to any appropriate procedure in which it is desirable to stiffen a distal end of an assembly. Therefore, it will be understood that the following discussions are not intended to limit the scope of the appended claims.

With reference to FIG. 1, an exemplary catheter assembly, guide wire, sensing catheter or mapping catheter 8 is shown. The mapping catheter 8 can be employed in any procedure in which it is desired to measure or sense the electrical activity of a structure. In one example, the mapping catheter 8 can be used to sense the electrical activity of a portion of the heart muscle. In addition, it should be noted that the exemplary mapping catheter 8 can be used in combination with other medical systems and devices and, for example, can be used with a tissue ablation device, such as the Arctic Front®, which is commercially available from CryoCath Technologies, Inc. of Kirkland, Quebec, Canada. Furthermore, the teachings of the present disclosure can be utilized in conjunction with the systems and methods disclosed in co-pending U.S. patent application Ser. No. 11/021,113 (filed on Dec. 22, 2004), Ser. No. 12/199,016 (filed on Aug. 27, 2008) and Ser. No. 12/199,255 (filed on Aug. 27, 2008), which are herein incorporated by reference in their entirety.

Figure 2:
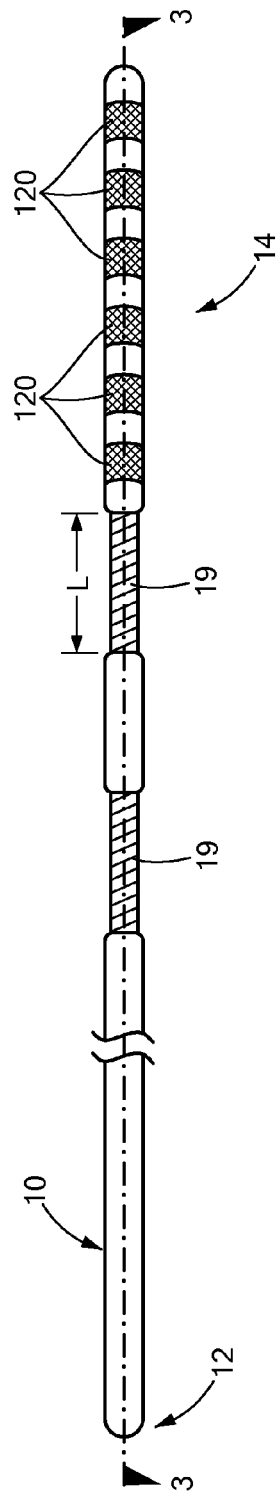
FIG. 2 is a schematic illustration of the exemplary catheter assembly of FIG. 1 in a second configuration.
Figure 3:
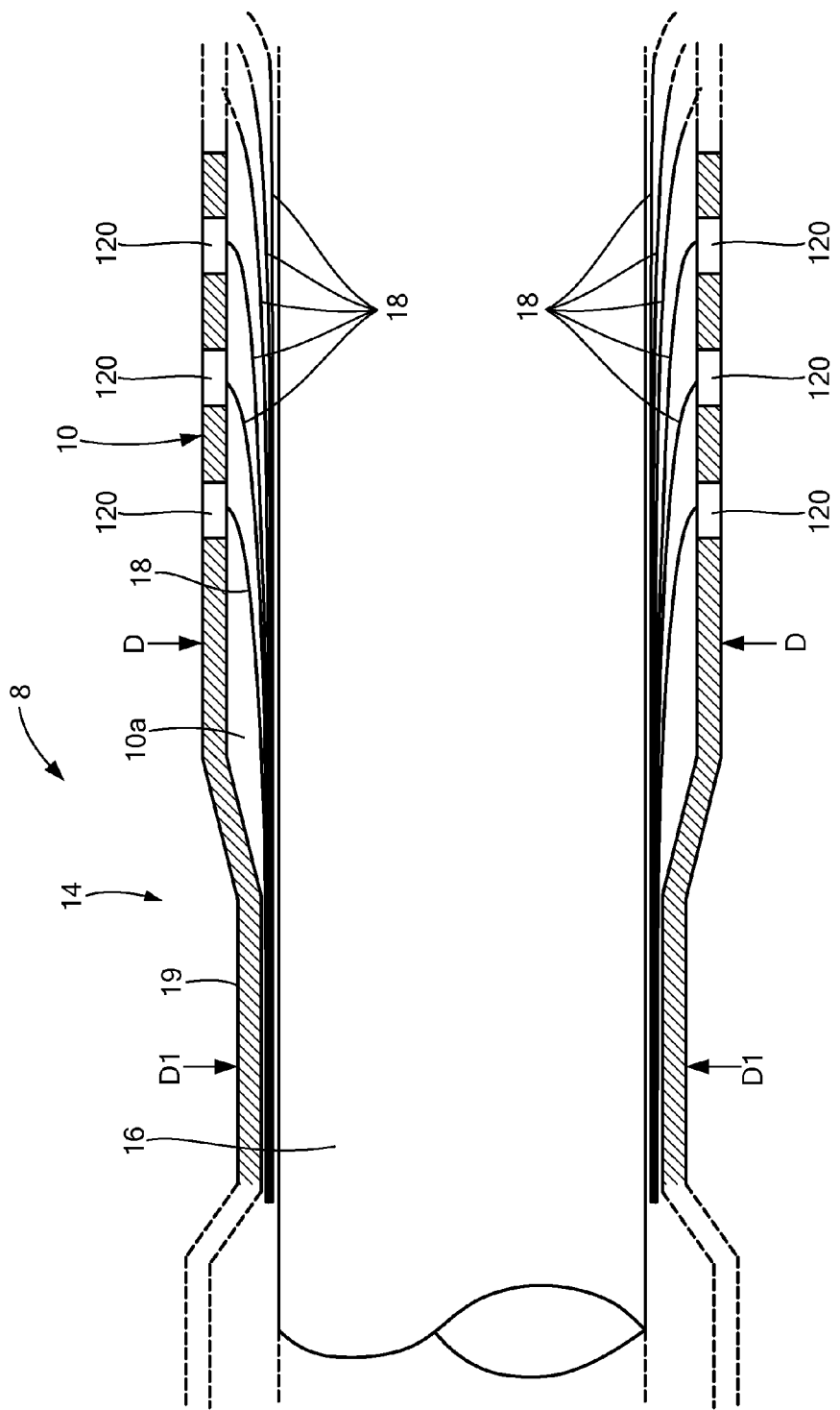
FIG. 3 is a cut-away schematic illustration of the exemplary catheter assembly of FIG. 1, taken along line 3-3 of FIG. 2.

With reference to FIGS. 1-3, the mapping catheter 8 can include a body 10, a proximal end 12, a distal end 14, a core wire 16 (FIG. 3) and a necked portion 19. The body 10 can generally define an elongated tubular structure, which can be comprised of any suitable biocompatible material, such as a biocompatible polymer. In one example, the body 10 can be composed of a polyether block amide, such as Pebax®, commercially available from Arkema of France. The body 10 can have a diameter D that is from about 0.014 inches to about 0.042 inches in size. In one example, the diameter D of the body 10 can be sized so that the mapping catheter 8 can be slidably received through a lumen defined in a tissue ablation device, however, it should be understood that the mapping catheter 8 can have any suitable diameter. With reference to FIG. 3, the body 10 can define a lumen 10a, which can extend from the proximal end 12 to the distal end 14. In one example, the lumen 10a can be closed at the distal end 14 and open at the proximal end 12, however, the lumen 10a could be open at both the proximal end 12 and the distal end 14 to enable an instrument to pass there through, such as a guide wire.

With reference to FIGS. 1-3, as the proximal end 12 and the distal end 14 of the mapping catheter 8 can be substantially similar to the proximal end and distal end of the guide wire described in co-pending U.S. patent application Ser. No. 12/199,016 and will, therefore, not be described in great detail herein. Briefly, the proximal end 12 of the mapping catheter 8 can be grasped by a user, such as a surgeon, to enable the surgeon to manipulate the mapping catheter 8. Although not illustrated herein, the proximal end 12 can include a graspable portion, such as a handle or protrusion, if desired.

The distal end 14 can include the one or more sensing electrodes 120. The electrodes 120 can be annular, and generally can be coupled circumferentially about the distal end 14 of the mapping catheter 8. It should be noted that although the mapping catheter 8 is illustrated herein as including six electrodes 120, the mapping catheter 8 can include any desired number of electrodes, such as one. The electrodes 120 can transmit sensed electrical activity over at least one lead 18. The at least one lead 18 can be in communication with a mapping system coupled to the proximal end 12 of the mapping catheter 8, for example, which can analyze and display the electrical activity for the surgeon. The distal end 14 can be movable from a first configuration (FIG. 1) to a second configuration (FIG. 2) to enable the mapping catheter 8 to be placed adjacent to or positioned within a pulmonary vein, to sense the electrical activity about a circumference of the pulmonary vein, for example.

The core wire 16 can enable the distal end 14 of the mapping catheter 8 to move from the first configuration (FIG. 1) to the second configuration (FIG. 2). In this regard, the core wire 16 can be received within the lumen 10a of the body 10, and can composed of any suitable biocompatible material, such as a shape memory biocompatible metal or metal alloy. In one example, the core wire 16 can be composed of a nickel titanium alloy, such as Nitinol. As is known, the use of a shape memory material can enable the core wire 16 to move from a first configuration or shape (FIG. 1) to a second configuration or shape (FIG. 2). In various embodiments, the movement of the mapping catheter 8 from a first configuration or shape (FIG. 1) to a second configuration or shape (FIG. 2) can be effectuated with the use of pull wire(s) or other mechanical device, or the use of electrically actuated wires that change shape when current or voltage is applied thereto. In one example, a portion of the core wire 16 at the distal end 14 can be shaped into a pigtail, as illustrated in FIG. 1, to enable the mapping catheter 8 to sense electrical activity about a circumference of a pulmonary vein, for example.

With reference to FIG. 3, the necked portion 19 can be formed at the distal end 14 of the mapping catheter 8. More specifically, in various embodiments the necked portion 19 can be formed adjacent to the distal end 14 that can be shaped into a pigtail, as illustrated in FIG. 1. Furthermore, while the illustrated mapping catheter 8 includes one necked portion 19, it is contemplated that the mapping catheter 8 can include a plurality of necked portions 19 at various locations along the longitudinal length of body 10.

The necked portion 19 can have a diameter D1 that is slightly smaller than the diameter D of the body 10. In various embodiments, the diameter D1 can be between 0.8-1.0 millimeters or, more specifically, approximately 0.9 millimeters. Generally, with reference to FIG. 1, the necked portion 19 can extend for a length L, which can be less than or about equal to a length L1 from the necked portion 19 to the proximal end 12. In various embodiments, the length L can be between 5-20 centimeters or, more specifically, between 8-12 centimeters.

With reference back to FIG. 3, the necked portion 19 can provide additional stiffness to the distal end 14 of the mapping catheter 8, and can also provide additional support to an instrument coupled over the mapping catheter 8, such as a tissue ablation device. For example, the formation of the necked portion 19 can increase the stiffness of the distal end 14 of the mapping catheter 8 by about 20 to over 200 percent.

The necked portion 19 can be formed by the application of at least heat to an assembled mapping catheter 8. In one example, the necked portion 19 can be formed by passing at least a portion of an assembled mapping catheter 8 through a heat source or heated mold, such as through an Auto-Necker Heated Die Tubing Necker, commercially available from Beahm Designs of Campbell, Calif., USA. The application of heat to at least a portion of the distal end 14 of the mapping catheter 8 can cause the body 10 to shrink about the core wire 16 and the at least one lead 18 to form the necked portion 19.

In various embodiments, the necked portion 19 can be formed methods other than the application of heat. For example, necked portion 19 can be formed by injection of an adhesive or other curable substance, e.g., silicon, into a desired location along the catheter body 10. Once cured, the adhesive can cause the body 10 to bond to and/or shrink about the core wire 16 and the at least one lead 18 to form the necked portion 19. In other embodiments, the necked portion 19 can be formed by wrapping a filament or other wrapping material around the body 10 in order to compress the body 10 about the core wire 16.

Figure 4:
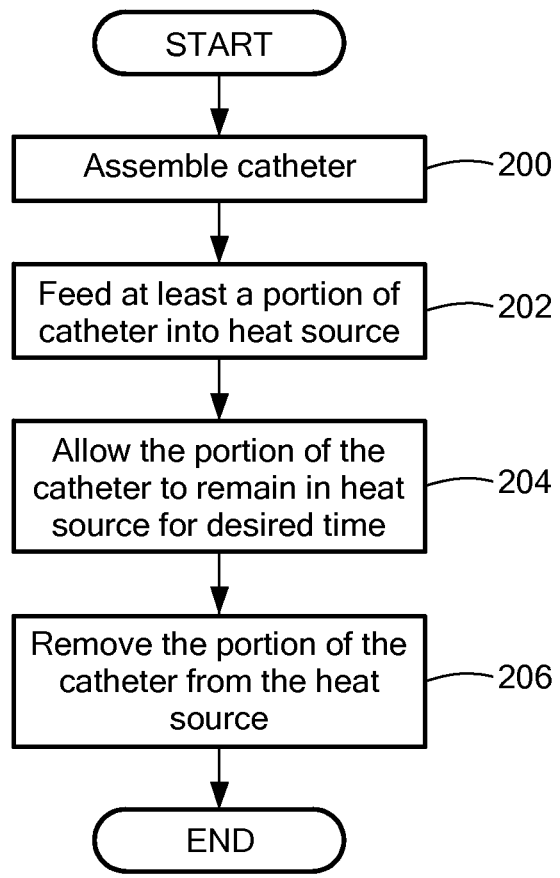
FIG. 4 is a simplified flow diagram illustrating an exemplary method of forming the exemplary catheter assembly of FIG. 1.

In this regard, with reference to FIG. 4, a flow diagram illustrates an exemplary method for forming the necked portion 19. At block 200, the mapping catheter 8 can be assembled, by securing the electrodes 120 to the body 10, and positioning the core wire 16 within the lumen 10a. At block 202, at least a portion of the mapping catheter 8 can be positioned into a heat source. For example, as discussed, at least a portion of the distal end 14 of the mapping catheter 8 can be received into the Auto-Necker Heated Die Tubing Necker, commercially available from Beahm Designs of Campbell, Calif., USA.

Next, at block 204, the portion of the distal end 14 of the mapping catheter 8 can remain within the heat source for a desired period of time. Generally, the portion of the distal end 14 of the mapping catheter 8 can remain within the heat source for a period of time sufficient enough to enable the body 10 to shrink about the core wire 16, thereby forming the necked portion 19. In one example, in the case of a feed-through heat source, the distal end 14 of the mapping catheter 8 can be advanced or fed through the heat source at a feed rate from about one millimeter per second (mm/s) to about six mm/s. It should be understood, however, that these times can vary depending upon the heat source employed and the composition of the body 10. At block 206, the portion of the mapping catheter 8 can be removed from the heat source.

While specific examples have been described in the specification and illustrated in the drawings, it will be understood by those of ordinary skill in the art that various changes can be made and equivalents can be substituted for elements thereof without departing from the scope of the present disclosure. Furthermore, the mixing and matching of features, elements and/or functions between various examples is expressly contemplated herein so that one of ordinary skill in the art would appreciate from this disclosure that features, elements and/or functions of one example can be incorporated into another example as appropriate, unless described otherwise, above. Moreover, many modifications can be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description.

What is claimed is:

1. A catheter assembly for use in an anatomy comprising:
   an elongated body having body wall, a proximal end defining a first outer diameter, and a distal end defining a second outer diameter, and defining a lumen from the proximal end to the distal end;
   at least one electrode coupled to the distal end that senses an electrical activity within the anatomy;
   a core wire received within the lumen extending from the proximal end to the distal end and bonded with at least a portion of the elongate body, the core wire configured to move the distal end from a first configuration to a second configuration; and
   a necked portion formed between the proximal end and the distal end and providing increased stiffness to the distal end of the body, the necked portion having a third outer diameter that is less than each of the first and second outer diameters, and a thickness of the body wall of the elongate body being the same in the proximal end, the necked portion, and the distal end.

2. The catheter assembly of claim 1, wherein the first configuration includes a substantially helical shape.

3. The catheter assembly of claim 1, wherein the necked portion includes a necked diameter smaller than a body diameter of the elongated body.

4. The catheter assembly of claim 1, wherein the elongated body bonds with the core wire at the necked portion.

5. The catheter assembly of claim 3, further comprising a second necked portion formed between the proximal end and the distal end.

6. The catheter assembly of claim 1, further comprising a second necked portion formed between the proximal end and the distal end to provide increased stiffness to the body.

7. The catheter assembly of claim 1, wherein the necked portion has a longitudinal length of between 5 and 20 centimeters.

8. The catheter assembly of claim 1, wherein the necked portion has a necked diameter of between 0.8 and 1.0 millimeters.

9. The catheter assembly of claim 1, wherein the core wire moves the distal end from a first configuration to a second configuration by shape memory metal.

10. The catheter assembly of claim 1, wherein the core wire moves the distal end from a first configuration to a second configuration by pull wire.

11. A catheter assembly for use in an anatomy comprising:
    an elongated body having a body wall, a proximal end, a distal end, and a body diameter, and further defining a lumen from the proximal end to the distal end;
    a plurality of electrodes coupled to the distal end configured to sense an electrical activity within the anatomy;
    a core wire received within the lumen extending from the proximal end to the distal end, the core wire configured to move the distal end from a first configuration to a second configuration;
    at least one necked portion formed between the proximal end and the distal end and providing increased rigidity to the distal end of the body wherein the at least one necked portion has a necked diameter smaller than the body diameter, a thickness of the body wall of the elongate body being the same in the proximal portion, the at least one necked portion, and the distal portion;
    the core wire being directly bonded to the elongate body at the at least one necked portion.

* * * * *

UNITED STATES PATENT AND TRADEMARK OFFICE
CERTIFICATE OF CORRECTION

| | | |
|---|---|---|
| PATENT NO. | : 8,929,969 B2 | Page 1 of 1 |
| APPLICATION NO. | : 12/533264 | |
| DATED | : January 6, 2015 | |
| INVENTOR(S) | : Edward M. Gillis and Christine Beltran | |

It is certified that error appears in the above-identified patent and that said Letters Patent is hereby corrected as shown below:

In the Claims

In Column 5, line 20, Claim 1, after "body having" add --a--.

In Column 6, line 16, Claim 9, replace "a" in two places with --the--.

In Column 6, line 19, Claim 10, replace "a" in two places with --the--.

Signed and Sealed this
Fifteenth Day of September, 2015

Michelle K. Lee
*Director of the United States Patent and Trademark Office*